(12) United States Patent
Elsik et al.

(10) Patent No.: US 8,288,317 B2
(45) Date of Patent: Oct. 16, 2012

(54) LIQUID CRYSTAL AGROCHEMICAL FORMULATIONS

(75) Inventors: Curtis M. Elsik, The Woodlands, TX (US); Joe C. Arzola, Austin, TX (US); Howard M. Stridde, George West, TX (US); Alan Stern, Magnolia, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 528 days.

(21) Appl. No.: 12/444,477

(22) PCT Filed: Oct. 9, 2007

(86) PCT No.: PCT/US2007/080764
§ 371 (c)(1),
(2), (4) Date: Apr. 6, 2009

(87) PCT Pub. No.: WO2008/045850
PCT Pub. Date: Apr. 17, 2008

(65) Prior Publication Data
US 2010/0105559 A1    Apr. 29, 2010

Related U.S. Application Data

(60) Provisional application No. 60/828,715, filed on Oct. 9, 2006.

(51) Int. Cl.
| | | |
|---|---|---|
| A01N 57/18 | (2006.01) |
| A01N 39/02 | (2006.01) |
| A01N 37/22 | (2006.01) |
| A01N 33/18 | (2006.01) |
| A01N 43/64 | (2006.01) |
| A61K 31/535 | (2006.01) |
| A61K 31/44 | (2006.01) |
| A61K 31/41 | (2006.01) |

(52) U.S. Cl. ........ 504/206; 504/323; 504/341; 504/342; 504/347; 514/229.2; 514/341; 514/383

(58) Field of Classification Search .................. None
See application file for complete search history.

(56) References Cited

U.S. PATENT DOCUMENTS

| | | | |
|---|---|---|---|
| 4,690,775 A | 9/1987 | Schott et al. | |
| 5,409,885 A | 4/1995 | Derian et al. | |
| 5,512,534 A | 4/1996 | Frisch et al. | |
| 5,547,918 A | 8/1996 | Newton et al. | |
| 6,093,681 A | 7/2000 | Ward et al. | |
| 6,117,820 A | 9/2000 | Cutler et al. | |
| 6,200,586 B1 | 3/2001 | Lambie et al. | |
| 6,407,042 B1 | 6/2002 | Ward et al. | |
| 6,770,612 B1 | 8/2004 | Hatchman | |
| 6,881,707 B2 * | 4/2005 | Howat et al. | 504/206 |
| 7,049,270 B2 * | 5/2006 | Lennon et al. | 504/206 |
| 2004/0009882 A1 | 1/2004 | Elsik et al. | |
| 2005/0261130 A1 | 11/2005 | Lennon et al. | |
| 2006/0194699 A1 | 8/2006 | Moucharafieh et al. | |
| 2007/0027034 A1 | 2/2007 | Tank et al. | |

* cited by examiner

*Primary Examiner* — Alton Pryor
(74) *Attorney, Agent, or Firm* — Huntsman International LLC (57) ABSTRACT

An agrochemical composition includes a homogeneous single-phase liquid crystal in thermodynamic equilibrium. The agrochemical composition can be a surfactant composition or a pesticide composition. The surfactant composition is a blend of surfactants, whereas a pesticide composition has an active ingredient and one or more surfactant adjuvants. A pesticide composition, or a surfactant composition in combination with an active ingredient, may be used to control pests.

21 Claims, 2 Drawing Sheets

LIQUID CRYSTAL AGROCHEMICAL FORMULATIONS

CROSS-REFERENCE TO RELATED APPLICATIONS

This application is the National Phase of International Application PCT/US2007/080764 filed Oct. 9, 2007 which designated the U.S. and which claims priority to U.S. Provisional App. Ser. No. 60/828,715 filed Oct. 9, 2006. The noted applications are incorporated herein by reference.

FIELD OF THE INVENTION

This invention relates to agrochemical formulations and more specifically to agrochemical formulations that include a homogeneous single-phase liquid crystal in thermodynamic equilibrium.

BACKGROUND OF THE INVENTION

Pesticide compositions have been used in agrochemical and related applications. Pesticide compositions typically include an active ingredient as well as one or more adjuvants. In some applications, an active ingredient is a herbicide such as glyphosate. An example of a typical adjuvant is a surfactant. Pesticide compositions are disclosed in U.S. Pat. No. 4,690,775; U.S. Pat. No. 5,409,885; U.S. Pat. No. 5,512,534; U.S. Pat. No. 5,547,918; U.S. Pat. No. 6,093,681; U.S. Pat. No. 6,117,820; U.S. Pat. No. 6,200,586; U.S. Pat. No. 6,407,042; U.S. Pat. No. 6,770,612; U.S. Pat. No. 7,049,270; and U.S. Patent Application Publications No. 2005/0261130 A1 and No. 2007/0027034A1.

There are many kinds of pesticide compositions. For instance, conventional pesticide compositions may include a dispersion of spherulites or discontinuous drops of liquid crystal material. Such spherulites may be used to suspend a solid active ingredient as a dispersion. Other conventional pesticide compositions include aqueous mixtures and dispersions that may depend on lipophilic alcohol molecules. Such alcohols are not surfactants. Yet other conventional pesticide compositions may be an emulsion such as an emulsion of oil and water that may have liquid crystalline material at the oil/water interface. Such liquid crystalline material is a dispersed liquid crystal phase, and these emulsions are not in thermodynamic equilibrium. Further conventional compositions include a structured aqueous system that forms as a gel and may be precipitated as a second phase out of a first phase. Such system is a dispersion of liquid crystal material. Additional compositions include a gel obtained by centrifuging an emulsion system. These emulsions are not in thermodynamic equilibrium, and the gels are typically an isotropic gel. Generally, if a pesticide composition is isotropic it does not exhibit birefringence whereas if a pesticide composition is anisotropic it does exhibit birefringence. The arrangement of liquid crystals in a pesticide can affect birefringence.

Conventional surfactants typically form liquid crystals when highly concentrated above 40 w/w % surfactant. For example, conventional pesticide compositions may form anisotropic aggregates, or two-phase dispersions, of liquid crystals on a wax paper or plant surface (e.g., after spraying) when a solution such as a spray solution becomes highly concentrated in surfactant. This liquid crystal phase may form as discontinuous regions dispersed in a continuous isotropic concentrated spray solution. Such concentrated pesticide formulations are not birefringent homogeneous liquid crystals in a single thermodynamic equilibrium phase.

Drawbacks to conventional agrochemical compositions include that the surfactants are typically not formulated as a single-phase thermodynamic equilibrium liquid crystal. Multiple phase systems will have physical instabilities and can only be kinetically stable. Additional drawbacks to such agrochemical compositions include retention of the spray drops on the target surface and incomplete incorporation into the target pest. Further drawbacks include the limited time the active ingredient has to move into the pest due to the spray solution solidifying. Drawbacks to standard single-phase liquid crystal formulations include a high load of surfactant and high viscosity.

Consequently, there is a need for an improved agrochemical composition. Further needs include an improved pesticide composition that exists or has a thermodynamically stable homogeneous liquid crystal phase. Important needs for a liquid crystal formulation include both a relatively low surfactant concentration and a relatively low viscosity. Additional needs include a pesticide composition having improved retention and improved time for active ingredient diffusion.

BRIEF SUMMARY OF SOME OF THE PREFERRED EMBODIMENTS

These and other needs in the art are addressed in one embodiment by an agrochemical composition comprising an active ingredient and a surfactant adjuvant. In some embodiments, the agrochemical composition is a homogeneous single-phase liquid crystal in thermodynamic equilibrium. The formulation may include both relatively low surfactant concentration and relatively low viscosity.

The foregoing has outlined rather broadly the features and technical advantages of the present invention in order that the detailed description of the invention that follows may be better understood. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent constructions do not depart from the spirit and scope of the invention as set forth in the appended claims.

DETAILED DESCRIPTION OF THE PREFERRED EMBODIMENTS

In an embodiment, an agrochemical composition such as a pesticide composition, includes an active ingredient and a surfactant adjuvant, and it is a homogeneous single-phase liquid crystal in thermodynamic equilibrium. In some embodiments, the homogeneous single-phase liquid crystal in thermodynamic equilibrium may contain a solubilized oil phase. In alternative embodiments, the homogeneous single-phase liquid crystal in thermodynamic equilibrium does not contain a solubilized oil phase. In an embodiment in which the pesticide composition is substantially at rest, the pesticide composition is anisotropic, the surfactant molecules are oriented, and the solution exhibits birefringence. Such structuring may be monitored by any suitable method. In an embodiment, the structuring may be monitored by observing the system between cross polarized films. For instance, the liquid crystal system may be lit up in bright contrast to a dark isotropic phase when placed between cross polarized films.

An embodiment of the pesticide composition may have any form of homogeneous single-phase liquid crystal in thermodynamic equilibrium suitable for use in pesticide applications. Without limitation, examples of suitable forms include lamellar, expanded lamellar, cubic, hexagonal, and reverse hexagonal forms of the liquid crystal phase behavior.

Active ingredients may include any chemical substance that has pesticidal properties. Without limitation, examples of active ingredients having pesticidal properties include herbicides, insecticides, fungicides, biocides, molluscicides, algaecides, plant growth regulators, anthelmintics, rodenticides, nematocides, acaricides, amoebicides, protozoacides, or combinations thereof. Without limitation, further examples of such pesticides include triazine herbicides such as simazine, atrazine, terbuthylazine, terbutryn, prometryn and ametryn; urea herbicides such as diuron and fluometuron; sulfonyl urea herbicides such as chlorsulfuron, metsulfuron methyl, nicosulfuron and triasulfuron; sulfonanilide herbicides such as flumetsulam; organophosphate insecticides such as azinphos methyl, chlorpyrifos, sulprofos and azamethiphos; carbamate insecticides such as aldicarb, bendiocarb, carbaryl and fenobucarb; acid amide herbicides such as metolachlor and alachlor; fungicides such as dimethomorph, benomyl, carbendazim, mancozeb, fluoxastrobin, and tebuconazole; chlorophenoxy herbicides such as 2,4-D, 2,4-DB, MCPA, MCPB, and 2,4,5-T; triazolinone herbicides such as amicarbazone, carfentrazone-ethyl, and sulfentrazone; chloronicotinyl insecticides such as imidacloprid, thiacloprid, and acetamiprid; plant growth regulators such as flumetralin; and acaricides such as propargite. Lists of pesticides are disclosed in the Crop Protection Dictionary (contained in the Meisterpro Crop Protection Handbook) and the British Crop Protection Council: The Pesticide Manual, which are each incorporated herein by reference in their entirety. It is to be understood that the pesticide composition may include any combination of active ingredients suitable for a desired application. In an embodiment, the active ingredients include an herbicide such as glyphosate. In some embodiments, the active ingredients comprise glyphosate, one or more salts thereof, or combinations thereof. For example, in agricultural applications, acceptable glyphosate salts include potassium salts, isopropylamine salts, ammonium salts, sodium salts, and monoethanolamine (MEA) salts, although embodiments are not limited thereto.

In some embodiments, one or more active ingredients include an insecticide. In addition, in some embodiments the active ingredient includes a fungicide. In an embodiment, one or more of the active ingredients is formulated as a dispersion of solids that may remain suspended in the homogeneous single-phase liquid crystal in thermodynamic equilibrium.

The pesticide composition may contain any amount of the active ingredient (a.i.) suitable for a desired application. In an embodiment, the pesticide composition contains from about 0.01 w/w % to about 65.0 w/w % of the active ingredient, alternatively from about 5.0 w/w % to about 55.0 w/w % of the active ingredient. Ready-to-use products can contain very low a.i. loadings.

An embodiment of the pesticide composition may contain any surfactant adjuvant suitable for providing a pesticide composition having a homogeneous single-phase liquid crystal in thermodynamic equilibrium. In an embodiment, the surfactant adjuvant includes the phosphate ester of an ethoxylated surfactant. Without limitation, examples of suitable phosphate ester surfactants include the SURFONIC® PE-series phosphate ester surfactants. In some embodiments, the phosphate ester of an ethoxylated surfactant is the phosphate ester of an ethoxylated alcohol. Without limitation, examples of suitable ethoxylated alcohols include the SURFONIC® L-series linear alcohol ethoxylates, the SURFONIC® DA-series branched decyl alcohol ethoxylates and the SURFONIC® TDA-series branched tridecyl alcohol ethoxylates. All of the SURFONIC® surfactants are commercially available from Huntsman Corporation (The Woodlands, Tex.). Additional embodiments also include the surfactant adjuvant further comprising other surfactants such as an alkylpolysaccharide. A commercial example of an alkylpolysaccharide is TERWET® 3001 surfactant, which is commercially available from Huntsman Corporation. In another embodiment the surfactant adjuvant includes a canola dimethylaminopropylamine amidoamine oxide surfactant. Additional embodiments also include other surfactant chemistries such as a mono- or di-alkyl sulphosuccinate derivative, a nonionic alcohol alkoxylate surfactant, an anionic surfactant such as an alkylbenzene sulfonate, and an amine functional surfactant. Without limitation, examples of suitable amine functional surfactants include the SURFONIC® T-series tallowamine ethoxylate and SURFONIC® AGM-550 polyetheramine ethoxylate surfactants. It is to be understood that the surfactant adjuvant may include any one or combination of surfactants. In an embodiment, the surfactant adjuvant comprises a blend of a phosphate ester of an ethoxylated surfactant and an alkylpolysaccharide, alternatively the phosphate ester of an ethoxylated alcohol and an alkylpolysaccharide. An embodiment of the pesticide composition may contain any amount of surfactant adjuvant suitable for providing a pesticide composition having a homogeneous single-phase liquid crystal in thermodynamic equilibrium. In an embodiment, the pesticide composition contains from about 0.5 w/w % to about 20.0 w/w % of the surfactant adjuvants.

In an embodiment, the active ingredients are dispersed in an aqueous medium by any suitable means. For instance, the active ingredients may be dispersed by stirring, mixing, blending, and the like. In an additional embodiment, the active ingredients are dispersed in or as an oil phase in the homogeneous continuous liquid crystal phase. In an embodiment, the active ingredients are a solid dispersed in a homogeneous continuous liquid crystal phase.

In an alternative embodiment, the pesticide composition contains additional adjuvants. It is to be understood that an adjuvant refers to a subsidiary additive in a mixture that contributes to the effectiveness of the primary ingredient. In an embodiment, the additional adjuvants include an oil-based adjuvant. Any oil-based adjuvant suitable for use in agrochemical applications may be used. Without limitation, examples of suitable oil-based adjuvants include crop oils, crop oil concentrates, vegetable oils, modified vegetable oils, or combinations thereof. An embodiment of the pesticide composition may contain any amount of the oil-based adjuvant suitable for a desired use. In some embodiments, the oil-based adjuvant facilitates efficacy of the active ingredient. In an embodiment, the pesticide composition contains from about 1.0 w/w % to about 15.0 w/w % of additional adjuvants. Other examples of adjuvants (e.g., non oil-based) include silicon-based adjuvants, sticker adjuvants, extender adjuvants, plant penetrant surfactants, compatibility agent adjuvants, mineral control adjuvants, drift retardant adjuvants, defoaming agent adjuvants, thickener adjuvants, solvent adjuvants, and fertilizer-based adjuvants. In an embodiment, the pesticide composition does not contain an inert adjuvant.

An embodiment of the pesticide composition may also contain formulation aids. Without limitation, examples of suitable formulation aids include antifreeze, dyes, thickening agents, preservatives, anti-foaming agents, ultraviolet stabilizers, and pH adjusting agents. An embodiment of the pesticide composition may contain any amount of the formulation aids suitable for a desired application. In an embodiment, the pesticide composition may contain from about 0.1 w/w % to about 10.0 w/w % of the formulation aids.

In an embodiment, the pesticide composition is applied in any desirable applications such as in agricultural applications. For instance, an embodiment of the pesticide composition may be applied to control weeds, insects, and/or fungi. In addition, the pesticide composition may be applied to insects, crops, soils, and the like, although embodiments are not limited in this aspect. Embodiments of the pesticide composition may be applied by any suitable method. In some embodiments, the pesticide composition is applied directly to the target (e.g., the insect, soil, and/or crop) or it is diluted before such application.

In some embodiments, the pesticide composition is a glyphosate composition that comprises greater than about 30 w/w % glyphosate salt comprising a single glyphosate salt or a mixture of glyphosate salts and also comprising one or more surfactant adjuvants. In some embodiments, the pesticide composition is a highly loaded glyphosate composition comprising greater than about 40 w/w % glyphosate salt comprising either a single potassium glyphosate salt or a mixture of potassium and isopropylamine (IPA) glyphosate salts, the phosphate ester of an ethoxylated alcohol, and an alkylpolysaccharide. The potassium and IPA glyphosate salts may be in any ratio suitable for an agrochemical use. In an embodiment, the pesticide composition comprises a weight ratio of potassium to IPA glyphosate salt from about 1:99 to about 99:1.

In an embodiment, a surfactant composition is formulated without active ingredient. This surfactant composition can exist as a homogeneous single-phase liquid crystal in thermodynamic equilibrium. In some embodiments, the surfactant composition can be added directly to a spray tank with standard commercial pesticide formulations to create a spray tank dilution that forms a homogeneous liquid crystal phase when the spray solution dries. In some embodiments, additional adjuvants or inert ingredients can be formulated with these surfactant compositions that also exist as a liquid crystal phase. In an embodiment, the additional adjuvant comprises a spray oil. In an additional embodiment, the adjuvant comprises a water conditioner adjuvant. Combinations of adjuvants and/or inert ingredients can also be included in one package mix product.

A pesticide composition having a homogeneous single-phase liquid crystal in thermodynamic equilibrium has many advantages over conventional compositions. For instance, the system is in a single-phase thermodynamic equilibrium, which provides long term physical stability vs. non-thermodynamic or multiple-phase equilibrium systems. Further advantages may include increased efficacy due to enhanced translocation of the active ingredient, drift control due to increased elongation viscosity of the spray solution, increased active ingredient diffusion resulting from keeping the spray from solidifying for extended times, and improved sticking of the spray solution to the target pest resulting from the surface chemistry of the surfactant phase behavior. Further advantages may include that a spray solution that forms a liquid crystal during drying much faster than an isotropic system that began with spherical micelles. Without being limited by theory, such further advantages may occur because the system being sprayed began as a liquid crystal. Additional advantages include that the entire spray solution will form a single-phase homogeneous liquid crystal during drying, since the formulation concentrate itself is a single-phase homogeneous liquid crystal. It should be noted that embodiments are not limited to a dispersion of anisotropic aggregates. Further advantages of an embodiment include that the liquid crystal phase may increase retention of the spray drop on the target surface due to increased viscosity of the spray solution. In addition, advantages include that a thermodynamic equilibrium phase may result in better long term physical stability than a product formulated as a non-equilibrium system that has only kinetic stability such as an emulsion or dispersion.

To further illustrate various illustrative embodiments of the present invention, the following examples are provided.

EXAMPLES

Example 1

According to an embodiment of the present invention, a pesticide composition exhibits birefringence and it forms a single-phase homogeneous liquid crystal in thermodynamic equilibrium. In a particular embodiment, the pesticide composition includes a mixed potassium:IPA salt of glyphosate with a high ratio of potassium together with a surfactant blend of two surfactants. One surfactant can be an experimental phosphate ester of an alcohol ethoxylate and another surfactant can be TERWET® 3001 alkylpolysaccharide.

The experimental phosphate ester of an alcohol ethoxylate was obtained from Huntsman Corporation and TERWET® 3001 alkylpolysaccharide is commercially available from Huntsman Corporation.

Referring to Table 1, below, several formulations are listed that included potassium glyphosate (58.0 w/w % active ingredient or potassium glyphosate, which corresponds to 47.5 w/w % acid equivalent (ae)) as an active ingredient. Formulations 1, 2, 3, and 6 also included IPA glyphosate (62% ai) as an active ingredient. That is, formulations No. 1-3 and 6 were mixed salt glyphosate formulations, whereas formulations No. 4 and 5 were single glyphosate salt formulations. All of these formulations are soluble liquid formulations. Potassium and isopropylamine (IPA) glyphosate salts are available from sources such as Monsanto (St. Louis, Mo.), Nufarm (Victoria, Australia), Albaugh (Ankeny, Iowa), or Cheminova (Lemvig, Denmark). Alternatively, potassium glyphosate may be prepared by neutralizing n-phosphonomethylglycine acid with potassium hydroxide, and IPA glyphosate may be prepared by neutralizing n-phosphonomethyl glycine acid with isopropylamine.

Each formulation listed in Table 1 also included Surfactant PESB5, an experimental phosphate ester of a blend of alcohol ethoxylates and TERWET® 3001 alkylpolysaccharide. A diethylene glycol (DEG) was also added to each formulation. The DEG used in the Formulations of Table 1 is commercially available from Huntsman Corporation. SURFONIC® T-5 is a surfactant that was added to Formulation 5; SURFONIC® T-5 is the 5-mole ethylene oxide (EO) tallow amine ethoxylate, which is also commercially available from Huntsman Corporation.

Generally, the formulations of Table 1 were made by mixing one or more glyphosate salts and surfactants in a sample bottle until uniform. In some instances, a sample was heated to facilitate mixing and cooled to room temperature (RT).

Preferably, glyphosate formulations meet several screening criteria before they are considered for commercial introduction. For instance, such criteria include that the formulation is physically stable, homogeneous at specified temperatures, has a cloud point typically greater than 50 degrees Celsius (° C.), and has a viscosity low enough to be pumped or poured. Thus, the glyphosate formulations of Table 1 were analyzed for homogeneity and cloud point. Homogeneity was established by visually inspecting the formulations at room temperature (RT) for clarity. Cloud point was determined by mixing each formulation while heating until it became cloudy. The formulation was then removed from the heat source and the temperature was measured in ° C. when the formulation regained clarity. The formulations of Table 1 were also examined to see if they exhibited birefringence. The birefringence of a formulation was established by visually inspecting a sample bottle containing the formulation that was placed between two cross-polarized plates. The cross-polarized plates were lighted from behind. The results for Formulations 1-6 are indicated in Table 1.

TABLE 1

| Ingredient | Formulation No. | | | | | |
|---|---|---|---|---|---|---|
| (grams) | 1 | 2 | 3 | 4 | 5 | 6 |
| K Glyphosate (58% ai) | 83.1 | 83.1 | 83.1 | 83.6 | 83.6 | 83.1 |
| IPA Glyphosate (62% ai) | 4.5 | 4.5 | 4.5 | — | — | 4.5 |
| TERWET 3001 | 6.2 | 5.8 | 5.4 | 5 | 7.5 | 6.6 |
| Surfactant PESB5 | 3.6 | 4 | 4.4 | 2.8 | 4.3 | 3.2 |
| SURFONIC T-5 | — | — | — | — | 2 | — |
| DEG | 1 | 1 | 1 | 1 | 1 | 1 |
| Water | 1.6 | 1.6 | 1.6 | 7.6 | 1.6 | 1.6 |
| Total w/w % | 100 | 100 | 100 | 100 | 100 | 100 |
| RT Solution Clear? | Y | Y | Y | Y | Y | Y |
| Cloud Point, (° C.) | 76 | 64 | 43 | 92 | 59 | 59 |
| Liquid Crystal? | Y | Y | Y | Y | Y | Y |

Figure 1:
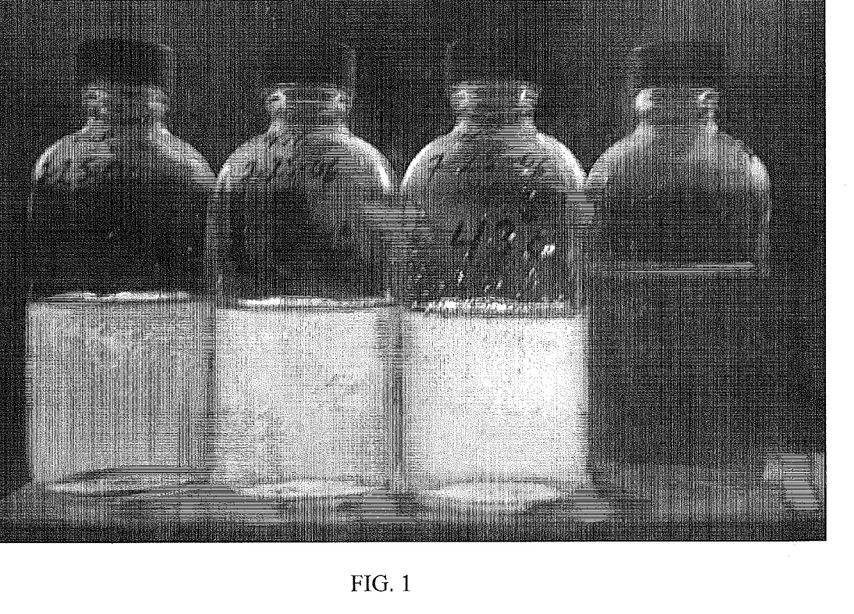
FIG. 1 shows exemplary embodiments that exhibit birefringent liquid crystal phases as compared to a sample having an isotropic phase.

Formulations No. 1, 2, 4, 5, and 6 had acceptable cloud points for a commercial product and Formulations No. 1-6 showed birefringence. For example, referring to FIG. 1, Formulations No. 1, 2, and 3 (from left to right) and a comparative isotropic sample (far right) were set between cross-polarized films that were lighted from behind. The three formulations on the left are bright as compared to the dark comparative on the right. Thus, the bright formulations exhibit birefringence, which indicates that they are anisotropic. In contrast, the comparative on the right is dark, which indicated that it is isotropic. Similar results were obtained for Formulations 4-6.

Figure 2:
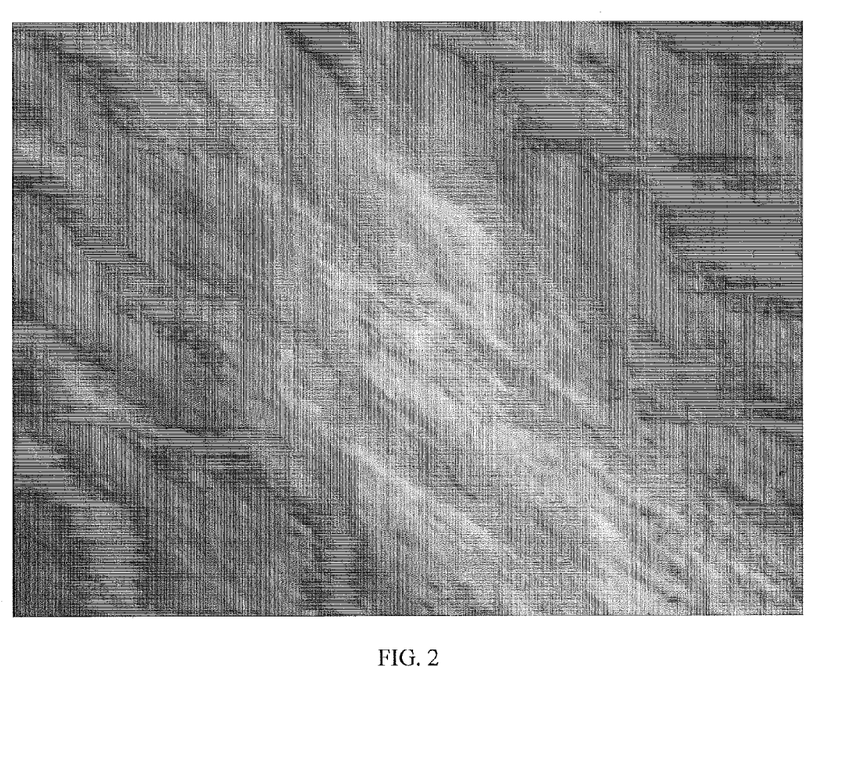
FIG. 2 is a cross-polarized light photomicrograph of an embodiment.

Referring to FIG. 2 a cross-polarized light photomicrograph of Formulation No. 2 is shown. The photomicrograph shows a uniform birefringence, not a dispersion of spherulites or discontinuous anisotropic aggregates in a continuous isotropic phase (which would be seen as bright particles dispersed in a dark continuous field on the photomicrograph). Thus, Formulation No. 2 was a homogeneous single-phase liquid crystal in thermodynamic equilibrium. This was surprising since the surfactant concentration in the formulations is relatively low, and the formulations all had relatively low viscosities and were pourable; the formulations all had acceptable viscosity for a commercial product. Similar results were obtained for Formulations No. 1 and 3-6; each formulation was a homogeneous single-phase liquid crystal in thermodynamic equilibrium.

Figure 3:
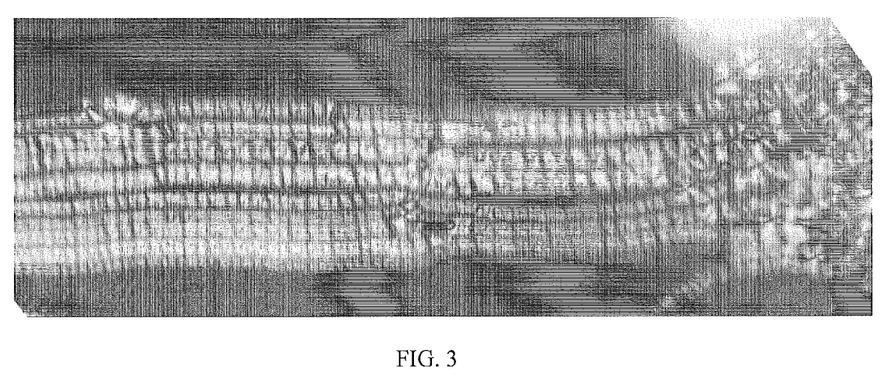
FIG. 3 shows an embodiment that is dried on a glass slide.

Referring to FIG. 3, Formulation No. 2 is shown after it was dried on a glass slide. Notably, the formulation formed a homogeneous, continuous liquid crystal and not a dispersion of anisotropic aggregates. For example, the dark areas of FIG. 3 are air bubbles from when the sample was applied to the slide. Furthermore, the physical morphology shows oily streak defects, which are indicative of a single homogeneous lamellar liquid crystal phase. Formulation No. 2 did not exhibit voids of darkness in the sample, which would have been caused by an isotropic continuous phase if only dispersions of anisotropic aggregates had been present. Thus, an embodiment of a pesticide composition can produce a single, homogeneous liquid crystal phase in thermodynamic equilibrium; a separate isotropic phase is not present.

The density of both Formulations No. 4 and No. 5 was 1.36 g/mL. They were both loaded at 660 g/L active ingredient and 540 g/L acid equivalent glyphosate, making them both highly loaded formulations with 4.5 pounds/gallon acid equivalent glyphosate. Formulation No. 4 had a normal surfactant load of 120 g/L, and Formulation No. 5 had a full surfactant load of 200 g/L. Extra surfactant is sometimes formulated into glyphosate formulations to boost efficacy on hard to control weeds or for severe weather conditions. Even though the formulations were high-load glyphosate, they both had relatively low viscosities. The Brookfield viscosity (LV2 spindle and 60 rpm) for Formulation No. 4 was 212 centipoise, and for Formulation No. 5 it was 277 centipoise. Even the fully surfactant loaded Formulation No. 5 was pourable.

A field trial was run on Formulation No. 5 of Table 1, above, and Roundup® Original (RU Original) herbicide (which were both applied at half label rates) to test for phytotoxicity and glyphosate efficacy. Roundup® Original is obtainable from Monsanto (St. Louis, Mo.). Generally, plants were grown on test plots that were thirty feet long by ten feet wide and that included four thirty-inch width rows of plants. Three replicate test plots were used for each herbicide tested. The crop chosen for testing was a Roundup Ready® soybean (Monsanto, St. Louis, Mo.), which were at the trifoliate stage, approximately 12 inches tall. The weeds in the test plots were 6-12 inches tall. The weeds studied included Tall Waterhemp (AMATU), Common Cocklebur (XANST), and Dent Corn (ZEAMD). One set of test plots was left unsprayed to act as a control—to monitor prevailing weed growth. Formulations were applied using flat fan nozzles at 30 pounds per square inch gauge (prig) spray pressure and 10 gallons/acre spray volume. The plots were visually observed at 10, 19, and 27 days after treatment (DAT) to determine weed control. No soybean phytotoxicity was observed for any of the samples.

The results of the field trial are shown in Table 2, and weed control is reported as a percent (%) of control. Generally, the results were obtained by observing the growth of weeds on each plot and averaging the observations for the three test plots that were sprayed with a particular herbicide. This average was compared to the average growth of that weed type in the control plots. For example, if the growth of AMATU on the control plots is taken as 100%, Formulation No. 5 reduced the growth of that weed type by 60% at 10 and at 19 DAT. In other words, only 40% of AMATU was observed growing on the test plots sprayed with Formulation No. 5 as compared to the average of the test plots left unsprayed.

TABLE 2

| Days After Treatment | Glyphosate Formulation | Weed Control % | | |
|---|---|---|---|---|
| | | AMATU | XANST | ZEAMD |
| 10 | No. 5 | 60 | 77 | 75 |
| | RU Original | 47 | 90 | 83 |
| 19 | No. 5 | 60 | 93 | 83 |
| | RU Original | 45 | 100 | 95 |
| 27 | No. 5 | 53 | 100 | 99 |
| | RU Original | 47 | 100 | 100 |

As is shown in Table 2, Formulation No. 5 performed better at 10 DAT than RU Original in controlling AMATU (Tall Waterhemp) growth. Furthermore, both formulations were effective at controlling XANST (Common Cocklebur) and ZEAMD (Dent Corn) growth at 10 DAT. Similar results were observed at 19 DAT. Table 2 also shows that Formulation No. 5 maintained a better performance at 27 DAT than RU Original with respect to AMATU, and that both formulations were very effective at controlling the final overall growth of XANST and ZEAMD.

Example 2

In some embodiments of the present invention, the pesticide composition included a single salt of glyphosate together with a surfactant blend. In an embodiment one surfactant in the blend was the experimental phosphate ester of a blend of alcohol ethoxylates, PESB5, and another surfactant was TERWET® 3001 alkylpolysaccharide, as is described in connection with Example 1, above.

Referring to Table 3 below, the compositions of soluble liquid formulations 7-19 are given. The glyphosate, DEG, and SURFONIC T-5 used in one or more of these compositions are the same as that in Example 1. Furthermore, the formulations of Table 3 were made as described in Example 1.

TABLE 4

| Ingredient | Formulation No. | | | | | | |
|---|---|---|---|---|---|---|---|
| (grams) | 20 | 21 | 22 | 23 | 24 | 25 | 26 |
| K Glyphosate (58% ai) | 83.6 | 83.6 | 83.6 | 83.6 | 83.6 | 83.6 | 85 |
| TERWET 3001 | 7.5 | 7.5 | 5.2 | 5.2 | 5.2 | 7.5 | — |
| Surfactant PESB5 | 4.3 | 4.3 | 3 | 3 | 3 | 4.3 | — |
| SURFONIC AGM-550 | 2 | 2 | 2 | 1 | 1 | 1 | — |
| ADM Crude Glycerin | — | 1 | — | — | — | — | — |
| DEG | — | — | — | — | 1 | — | — |
| Canola DMAPA Amidoamine Oxide Surfactant | — | — | — | — | — | — | 15 |
| Water | 2.6 | 1.6 | 6.2 | 7.2 | 6.2 | 3.6 | — |
| Total w/w % | 100 | 100 | 100 | 100 | 100 | 100 | 100 |
| RT Solution Clear? Y/N | Y | Y | N | Y | Y | Y | Y |
| Cloud Point, (° C.) | 52 | 51 | — | 60 | 59 | 61 | 65 |
| Liquid Crystal? Y/N | Y | Y | — | Y | Y | Y | Y |

Formulations No. 20-21 and 23-26 were single-phase homogeneous liquid crystals in thermodynamic equilibrium at room temperature; they were clear at RT and birefringent. SURFONIC® AGM-550 surfactant is a polyetheramine ethoxylate that is commercially available from Huntsman Corporation. ADM crude glycerin is available from Archer Daniels Midland Company (Decatur, Ill.).

TABLE 3

| Ingredient | Formulation No. | | | | | | | | | | | | |
|---|---|---|---|---|---|---|---|---|---|---|---|---|---|
| (grams) | 7 | 8 | 9 | 10 | 11 | 12 | 13 | 14 | 15 | 16 | 17 | 18 | 19 |
| K glyph. (58% ai) | 83.6 | 83.6 | 83.6 | 83.6 | 83.6 | 83.6 | 83.6 | 83.6 | 83.6 | 83.6 | 83.6 | 83.6 | 83.6 |
| TERWET 3001 | 7.5 | 7 | 6.5 | 6.2 | 5.8 | 5.4 | 4.6 | 4.2 | 7 | 6.5 | 5 | 4.6 | 4.2 |
| Surfact. PESB5 | 4.3 | 4.8 | 5.3 | 3.6 | 4 | 4.4 | 3.2 | 3.6 | 4.8 | 5.3 | 2.8 | 3.2 | 3.6 |
| SURFONIC T-5 | — | — | — | — | — | — | — | — | 2 | 2 | 2 | 2 | 2 |
| DEG | 1 | 1 | 1 | 1 | 1 | 1 | 1 | 1 | 1 | 1 | 1 | 1 | 1 |
| Water | 3.6 | 3.6 | 3.6 | 5.6 | 5.6 | 5.6 | 7.6 | 7.6 | 1.6 | 1.6 | 5.6 | 5.6 | 5.6 |
| Total w/w % | 100 | 100 | 100 | 100 | 100 | 100 | 100 | 100 | 100 | 100 | 100 | 100 | 100 |
| RT Soln. Clear? | Y | Y | Y | Y | Y | Y | Y | Y | N | N | N | N | N |
| Cloud Point (° C.) | 86 | 65 | 46 | 85 | 70 | 52 | 69 | 50 | — | — | — | — | — |
| Liquid Crystal? | Y | Y | Y | Y | Y | Y | Y | Y | — | — | — | — | — |

Formulations No. 7-14 were all single-phase homogeneous liquid crystals in thermodynamic equilibrium at room temperature. All but No. 9 and No. 14 had cloud points above 50° C. Formulations No. 15-19 were not single-phase systems. At room temperature they were liquid crystalline phases in equilibrium with a second isotropic phase. When mixed, the formulations were cloudy due to the two phases, and they were birefringent due to the dispersed liquid crystal phase.

Example 3

In some embodiments of the present invention, surfactant chemistries other than those shown in Examples 1 and 2 can be used to formulate pesticides that exist as single-phase homogeneous liquid crystals in thermodynamic equilibrium. For example, referring to Table 4 there are several example formulations shown that have two additional surfactant chemistries included in the raw materials used.

The canola DMAPA amidoamine oxide surfactant was synthesized by combining canola oil (125 grams) with dimethylaminopropylamine (DMAPA) (49 grams) in a reactor vessel, and heating the mixture to 160° C. The heated mixture was stirred under a nitrogen atmosphere for 6 hours. Excess DMAPA was stripped out of the reactor by passing a stream of nitrogen over the reaction mixture while continuing to stir at 160° C. The mixture was cooled to 50° C., and 35% hydrogen peroxide solution (45 grams) was carefully added. After 1 hour of continuous stirring, the canola-amidoamine N-oxide was ready for use. DMAPA is available from Huntsman (The Woodlands, Tex.), hydrogen peroxide is available from Sigma-Aldrich (St. Louis, Mo.), and canola oil was obtained from H.E. Butt Grocery Company (San Antonio, Tex.).

Example 4

Embodiments of the present invention are not limited to mixing soluble liquids. For example, referring to Table 5, below, package mix products were used to make Formulations No. 27-33. Package mix products are formulations that contain more than one active ingredient. The package mix formulations of Table 5 use glyphosate as one active ingredient and Formulation No. 4 (Table 1, above) as the building block product. Another, different active ingredient was added to the base formulation in each of Formulation 27-33. For example, metolachlor, imidacloprid, fluoxastrobin, flumetralin, amicarbazone, tebuconazole, and 2,4-D acid were added to Formulations No. 27-33 respectively. These package mix example formulations are shown in Table 5. For each formulation shown in Table 5, the continuous phases were birefringent liquid crystals. Thus, these examples show several different formulation types are possible using this technology. When the added active ingredient was a solid, a dispersion in the continuous liquid crystal phase was formed. When the added active ingredient was an oil, it could either disperse as a discontinuous oil phase emulsion or the oil could be incorporated into the lipophilic layers of the lamellar liquid crystal phase.

TABLE 5

| Ingredient | Formulation No. | | | | | | |
|---|---|---|---|---|---|---|---|
| (grams) | 27 | 28 | 29 | 30 | 31 | 32 | 33 |
| K Glyphosate (58% ai) | 7.53 | 7.53 | 7.53 | 7.53 | 7.53 | 7.53 | 7.53 |
| TERWET 3001 | 0.45 | 0.45 | 0.45 | 0.45 | 0.45 | 0.45 | 0.45 |
| Surfactant PESB5 | 0.25 | 0.25 | 0.25 | 0.25 | 0.25 | 0.25 | 0.25 |
| DEG | 0.09 | 0.09 | 0.09 | 0.09 | 0.09 | 0.09 | 0.09 |
| Water | 0.68 | 0.68 | 0.68 | 0.68 | 0.68 | 0.68 | 0.68 |
| Metolachlor tech. | 1.00 | — | — | — | — | — | — |
| Imidacloprid tech. | — | 1.00 | — | — | — | — | — |
| Fluoxastrobin tech. | — | — | 1.00 | — | — | — | — |
| Flumetralin tech. | — | — | — | 1.00 | — | — | — |

TABLE 5-continued

| Ingredient | Formulation No. | | | | | | |
|---|---|---|---|---|---|---|---|
| (grams) | 27 | 28 | 29 | 30 | 31 | 32 | 33 |
| Amicarbazone tech. | — | — | — | — | 1.00 | — | — |
| Tebuconazole tech. | — | — | — | — | — | 1.00 | — |
| 2,4-D Acid tech. | — | — | — | — | — | — | 1.00 |
| Total (grams) | 10.00 | 10.00 | 10.00 | 10.00 | 10.00 | 10.00 | 10.00 |
| Continuous Phase Liquid Crystal? Y/N | Y | Y | Y | Y | Y | Y | Y |

Potassium glyphosate may be obtained from Monsanto (St. Louis, Mo.), Nufarm (Victoria, Australia), Albaugh (Ankeny, Iowa), or Cheminova (Lemvig, Denmark), or it may be prepared as explained above. Metolachlor may be obtained from Syngenta (Greensboro, N.C.) or DuPont (Newark, Del.), whereas Imidacloprid may be obtained from Bayer (Kansas City, Mo.) or Cheminova (Lemvig, Denmark). Fluoxastrobin may be obtained from Bayer (Kansas City, Mo.). Flumetralin may be obtained from Syngenta (Greensboro, N.C.). Amicarbazone may be obtained from Arvesta (San Francisco, Calif.). Tebuconazole may be obtained from Bayer (Kansas City, Mo.) or Makhteshim-Agan (New York, N.Y.). 2,4-D Acid may be obtained from Nufarm (Victoria, Australia), and Albaugh (Ankeny, Iowa). TERWET® 3001 surfactant and experimental Surfactant PESB5 are available from Huntsman (The Woodlands, Tex.).

Example 5

Embodiments of the present invention do not require glyphosate as an active ingredient; other individual active ingredients can also be formulated such that the pesticide includes a single-phase homogeneous liquid crystals in thermodynamic equilibrium. Referring to Table 6, example formulations having herbicides other than glyphosate, insecticides, and fungicides are shown.

TABLE 6

| Ingredient | Formulation No. | | | | | | | |
|---|---|---|---|---|---|---|---|---|
| (grams) | 34 | 35 | 36 | 37 | 38 | 39 | 40 | 41 |
| TERWET 3001 | 1.01 | 0.50 | 0.50 | 0.50 | 0.50 | 0.50 | 0.50 | 0.50 |
| Surfactant PESB5 | 0.56 | 0.28 | 0.28 | 0.28 | 0.28 | 0.28 | 0.28 | 0.28 |
| DEG | 0.20 | 0.10 | 0.10 | 0.10 | 0.10 | 0.10 | 0.10 | 0.10 |
| Ammonium Sulfate | 5.49 | 2.73 | 2.73 | 2.73 | 2.73 | 2.73 | 2.73 | 2.73 |
| Ethylene Glycol | 1.37 | 0.68 | 0.68 | 0.68 | 0.68 | 0.68 | 0.68 | 0.68 |
| Water | 11.27 | 5.61 | 5.61 | 5.61 | 5.61 | 5.61 | 5.61 | 5.61 |
| Metolachlor tech. | 0.10 | — | — | — | — | — | — | — |
| Imidacloprid tech. | — | 0.10 | — | — | — | — | — | — |
| Fluoxastrobin tech. | — | — | 0.10 | — | — | — | — | — |
| Flumetralin tech. | — | — | — | 0.10 | — | — | — | — |
| Amicarbazone tech. | — | — | — | — | 0.10 | — | — | — |
| Tebuconazole tech. | — | — | — | — | — | 0.10 | — | — |
| 2,4-D Acid tech. | — | — | — | — | — | — | 0.10 | — |
| Dicamba tech. | — | — | — | — | — | — | — | 0.10 |
| Total (grams) | 20.00 | 10.00 | 10.00 | 10.00 | 10.00 | 10.00 | 10.00 | 10.00 |
| Continuous Phase Liquid Crystal? Y/N | Y | Y | Y | Y | Y | Y | Y | Y |

The continuous phases of Formulations No. 34-41 were single-phase homogeneous liquid crystals. Ethylene glycol is commercially available from Huntsman Corporation. Dicamba technical may be obtained from Albaugh (Ankeny, Iowa), or BASF (RTP, NC). Ammonium sulfate may be obtained from Kalo, Inc. (Overland Park, Kans.). The availability of other ingredients is discussed above.

soybean oil is available from Helena Chemical (Memphis, Tenn.). SURFONIC® PE-2281 surfactant and SURFONIC® PE-1198 surfactant are commercially available from Huntsman Corporation (The Woodlands, Tex.). Other availabilities are discussed above.

TABLE 7

| Ingredient | Formulation No. | | | | | | | | | |
|---|---|---|---|---|---|---|---|---|---|---|
| (grams) | 42 | 43 | 44 | 45 | 46 | 47 | 48 | 49 | 50 | 51 |
| TERWET 3001 | 5.02 | 5.02 | 5.02 | 1.01 | 1.01 | 1.01 | 1.01 | 1.01 | 0.50 | 0.50 |
| Surfactant PESB5 | 2.82 | — | — | 0.56 | 0.56 | 0.56 | 0.56 | 0.56 | 0.28 | 0.28 |
| DEG | 0.97 | 0.97 | 0.97 | 0.20 | 0.20 | 0.20 | 0.20 | 0.20 | 0.10 | 0.10 |
| Ammonium Sulfate | 27.53 | 27.53 | 27.53 | 5.49 | 5.49 | 5.49 | 5.49 | 5.49 | 2.73 | 2.73 |
| Ethylene Glycol | 6.88 | 6.88 | 6.88 | 1.37 | 1.37 | 1.37 | 1.37 | 1.37 | 0.68 | 0.68 |
| Water | 56.78 | 56.78 | 56.78 | 11.27 | 11.27 | 11.27 | 11.27 | 11.27 | 5.61 | 5.61 |
| SURFONIC PE-2281 | — | 2.82 | — | — | — | — | — | — | — | — |
| SURFONIC PE-1198 | — | — | 2.82 | — | — | — | — | — | — | — |
| EXXSOL D-130 | — | — | — | 0.10 | — | — | — | — | — | — |
| Sun 8N | — | — | — | — | 0.10 | — | — | — | — | — |
| JEFFSOL AG 1555 | — | — | — | — | — | 0.10 | — | — | — | — |
| JEFFSOL AG 1730 | — | — | — | — | — | — | 0.10 | — | — | — |
| Methylated Soybean Oil | — | — | — | — | — | — | — | 0.10 | — | — |
| High Fructose Corn Syrup | — | — | — | — | — | — | — | — | 0.10 | — |
| TERMIX 5910 | — | — | — | — | — | — | — | — | — | 0.10 |
| Total (grams) | 100.0 | 100.0 | 100.0 | 20.00 | 20.00 | 20.00 | 20.00 | 20.00 | 10.00 | 10.00 |
| Continuous Phase Liquid Crystal? Y/N | Y | Y | N | Y | Y | Y | Y | Y | Y | Y |

Example 6

In some embodiments, a surfactant composition formulated without any active ingredients produces a single-phase homogeneous liquid crystal in thermodynamic equilibrium. An embodiment of a surfactant composition could be used as a tank mix adjuvant that is added to a spray tank dilution of any active ingredient or combination of active ingredients. An embodiment of a surfactant composition could also contain additional adjuvants included to improve the efficacy of the active ingredient or ingredients, or it could also contain inert ingredients included to improve the physical stability of the formulation. Examples of some embodiments of a surfactant composition are shown in Table 7. Embodiments, however, are not limited to the examples of Table 7. Referring to Table 7, each formulation includes water, the water conditioning agent ammonium sulfate, DEG and TERWET® 3001. Formulations 45-50 include crop oil penetration aids EXXSOL® D-130 oil, Sun 8N oil, JEFFSOL® AG 1555 propylene carbonate, JEFFSOL® AG 1730 morpholine amide, methylated soybean oil; high fructose corn syrup respectively; Formulation 51 includes the spreader/sticker TERMIX® 5910 adjuvant. Formulations 42 and 45-51 include the experimental surfactant PESB5 whereas Formulations 43 and 44 include the phosphate ester surfactants SURFONIC® PE-2281 and SURFONIC® PE-1198 respectively.

EXXSOL D-130 is a registered trademark of and available from ExxonMobil Chemicals (Houston, Tex.). JEFFSOL® AG 1555 propylene carbonate, JEFFSOL® AG 1730 morpholine amide, and TERMIX® 5910 adjuvant are commercially available from Huntsman Corporation. Sun 8N oil is available from Sunoco (Philadelphia, Pa.). High fructose corn syrup is available from Cargill (Eddyville, Iowa). Methylated Formulations No. 42-44 are examples with three different phosphate ester surfactants. Only two produce a single-phase homogeneous liquid crystal in thermodynamic equilibrium. All of the other adjuvant compositions with additional components were single-phase homogeneous liquid crystals in thermodynamic equilibrium. Formulations No. 42-43 and 45-51 could be added to spray tank dilutions to accelerate the formation of this liquid crystal phase as the sprayed mixture dries.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A pesticide composition comprising: an active ingredient and a surfactant adjuvant, wherein the pesticide composition is a homogeneous, anisotropic, single-phase liquid crystal in thermodynamic equilibrium, the pesticide composition exhibits birefringence, and the pesticide composition has a viscosity low enough to be pumped or poured, and wherein the active ingredient is selected from the group consisting of metolachlor, imidacloprid, fluoxastrobin, flumetralin, amicarbazone, tebuconazole, 2,4-D acid, dicamba, glyphosate, a glyphosate salt, and combinations thereof.

2. The pesticide composition of claim 1, wherein the pesticide composition is one of an herbicide, an insecticide, or a fungicide.

3. The pesticide composition of claim 1, wherein the surfactant adjuvant comprises a phosphate ester of an ethoxylated surfactant.

4. The pesticide composition of claim 3, wherein the surfactant adjuvant is a phosphate ester of an ethoxylated alcohol.

5. The pesticide composition of claim 4, wherein the surfactant adjuvant further comprises an alkylpolysaccharide.

6. The pesticide composition of claim 1, wherein the pesticide composition further includes another, different active ingredient.

7. The pesticide composition of claim 1, wherein the surfactant adjuvant further comprises a tallow amine ethoxylate.

8. The pesticide composition of claim 1, wherein the surfactant adjuvant further comprises a polyetheramine ethoxylate.

9. The pesticide composition of claim 1, wherein the pesticide composition further comprises glycerin or an ethylene glycol.

10. The pesticide composition of claim 1, wherein the pesticide composition is a soluble, pourable liquid having a surfactant load that is less than or equal to 20.0 w/w % of the pesticide composition.

11. The pesticide composition of claim 1, wherein the active ingredient is a solid dispersed in the continuous, homogeneous liquid crystal phase in thermodynamic equilibrium.

12. The pesticide composition of claim 1, wherein the active ingredient is an oil or is dissolved in an oil, said active ingredient dispersed as a liquid in a continuous homogeneous liquid crystal phase in thermodynamic equilibrium.

13. The pesticide composition of claim 1, wherein the active ingredient is an oil or is dissolved in an oil, said active ingredient incorporated into a lipophilic layer of a lamellar liquid crystal phase.

14. The pesticide composition of claim 1, wherein the surfactant adjuvant further comprises a canola dimethylaminopropylamine amidoamine oxide surfactant.

15. A composition comprising: an active ingredient and a surfactant adjuvant blend, wherein the surfactant adjuvant blend is a homogeneous single-phase liquid crystal in thermodynamic equilibrium, the composition is anisotropic, the composition exhibits birefringence, and the composition has a viscosity low enough to be pumped or poured, and wherein the active ingredient is selected from the group consisting of metolachlor, imidacloprid, fluoxastrobin, flumetralin, amicarbazone, tebuconazole, 2,4-D acid, dicamba, glyphosate, a glyphosate salt, and combinations thereof.

16. The composition of claim 15, wherein one of the surfactants in said surfactant adjuvant blend is an alkylpolysaccharide.

17. The composition of claim 16, wherein another surfactant in said surfactant adjuvant blend is a phosphate ester surfactant.

18. The composition of claim 17, wherein the phosphate ester is a phosphate ester of an alcohol ethoxylate.

19. The composition of claim 18, further including a crop oil penetration aid or a spreading aid.

20. A method of controlling pests by applying the pesticide composition of claim 1, wherein the pesticide composition is applied to the pest or pest's environment or diluted in a spray solution and applied to the pest or pest's environment.

21. A method of controlling pests by adding the composition of claim 15 to a spray tank dilution containing active ingredient, wherein the final combined spray tank mixture is adapted to be applied to the pest or pest's environment.

* * * * *